United States Patent [19]
Rubini et al.

[11] Patent Number: 5,939,351
[45] Date of Patent: *Aug. 17, 1999

[54] CATALYSTS AND CATALYST CARRIERS OBTAINED BY TABLETING

[75] Inventors: Carlo Rubini, Battaglia; Luigi Cavalli, Novara, both of Italy

[73] Assignee: Montecatini Technologie s.r.l., Italy

[*] Notice: This patent issued on a continued prosecution application filed under 37 CFR 1.53(d), and is subject to the twenty year patent term provisions of 35 U.S.C. 154(a)(2).

[21] Appl. No.: 08/615,959

[22] Filed: Mar. 14, 1996

[30] Foreign Application Priority Data

Mar. 14, 1995 [IT] Italy .................................. MI95A0486

[51] Int. Cl.$^6$ ..................................................... B01J 23/88
[52] U.S. Cl. .............................. 502/313; 502/305; 502/2; 502/8; 502/415; 502/321; 502/322; 502/338; 502/527
[58] Field of Search ................................ 502/305, 2, 313, 502/8, 415, 321, 322, 338, 527

[56] References Cited

U.S. PATENT DOCUMENTS

| | | | |
|---|---|---|---|
| 3,640,654 | 2/1972 | Smith | 425/78 |
| 4,016,106 | 4/1977 | Sawyer et al. | 252/455 R |
| 4,323,530 | 4/1982 | Voss et al. | 264/109 |
| 4,572,778 | 2/1986 | Ward | 208/89 |
| 4,707,309 | 11/1987 | Voss et al. | 264/12 |
| 4,818,743 | 4/1989 | Simpson et al. | 502/211 |
| 5,017,542 | 5/1991 | Martan et al. | 502/209 |
| 5,082,819 | 1/1992 | Boeck et al. | 502/212 |
| 5,330,958 | 7/1994 | Viola et al. | 502/316 |
| 5,330,959 | 7/1994 | Raby et al. | 502/201 |
| 5,399,535 | 3/1995 | Whitman | 501/80 |

FOREIGN PATENT DOCUMENTS

| | | |
|---|---|---|
| 0 095 851 | 5/1983 | European Pat. Off. |
| 0 355 664 | 8/1989 | European Pat. Off. |
| 0 417 722 | 9/1990 | European Pat. Off. |
| 0 394 677 | 10/1990 | European Pat. Off. |
| 0 464 633 | 6/1991 | European Pat. Off. |

OTHER PUBLICATIONS

Derwent Abstract and Family Search for European Patent No. 0 417 722. –no date.

Derwent Abstract and Family Search for European Patent No. 0 355 664. –no date.

*Primary Examiner*—Walter D. Griffin
*Assistant Examiner*—Nadine Preisch
*Attorney, Agent, or Firm*—Bryan Cave LLP

[57] ABSTRACT

Catalysts and catalyst carriers, in the form of granules having a definite geometric form, characterized by porosity values such that at least 70% of the volume of the pores have a radius corresponding to the peak values of the porosity distribution curve. The catalysts and catalyst carriers are obtained by compression shaping, wherein the lubricant employed is applied to the molding of the chamber (external lubrication).

17 Claims, 4 Drawing Sheets

CATALYSTS AND CATALYST CARRIERS OBTAINED BY TABLETING

The present invention regards granular catalysts and carriers having a definite geometric shapes and their preparation process. It refers in particular to granular catalyst and carriers having a complex geometric shape, as for example, a hollow cylindrical form with circular, polygonal or multi-lobed section.

The factors which influence the performance of a heterogeneous catalyst are manifold.

A granular catalyst suitable for use on a fixed bed generally satisfies at least the following prerequisites:
low resistance to fluid flow, i.e. low load loss;
high surface/volume ratios;
suitable mechanical resistance and resistance to abrasion so as to prevent the breakage or chalking of the catalyst.

The size and distribution of the pores play an important role in the performance of catalysts.

Cylindrical catalysts with small pores, thereby possessing large surface areas, on the one hand permit the reduction of reactor volume, but on the other may present problems in the diffusion of the reagents.

Catalysts with large pores and, therefore, with a small surface area, permit rapid diffusion of the reagents; they may, however, turn out to be inactive because of the limited area available. A bimodal distribution of the pore diameter represents a compromise solution.

The use of catalysts with a solid geometric form, because of the reduction in the empty spaces available, results in considerable losses of load in reactors in which the height of the fixed bed has to ensure high conversion speeds.

The necessity of working in conditions of turbulence so as to dispose of reaction heat results in further losses in load.

Catalysts of a hollow geometric form, as well as other advantages, permit the reduction in load loss which occur in the case of catalysts with a solid form. In the case of hollow cylindrical catalysts, the efficacy of the catalyst increases with the increase in the pore diameter with respect to the external diameter. However, increasing the diameter of the pores reduces the bulk of catalyst material available in the reactor.

Moreover, in the case of hollow catalysts considerable resistance to breakage and abrasion is required so as to avoid the undesirable formation of dusts.

Ideal catalysts having a hollow geometric form are those endowed with characteristics of high resistance to breakage and abrasion and which have such characteristics of porosity and pore dimensions as to permit a high exchange between the granules and the reaction fluids.

Catalysts of a hollow cylindrical form with a circular or polygonal multi-lobed section, endowed with through-bores in correspondence with the various lobes, are disclosed in U.S. Pat. No. 5,330,958.

These catalysts, as well as reducing load losses compared to the corresponding solid form catalysts, allow for the attainment, at a parity with bed volume, of higher yields.

Catalysts with a hollow cylindrical form or having another form are disclosed in the patent literature cited hereunder.

In EPA 95851 hollow cylindrical catalysts having at least three points of contact with a circumscribed cylindrical surface are disclosed.

The multitude of points of contact between the catalyst particles allow for the distribution of the charge exercised on the granules to several points, thereby reducing the tendency to breakage.

In EPA 417722 catalysts for the oxidation of olefins and unsaturated aldehydes are disclosed, having a cylindrical form with a circular, polygonal or multi-lobed section, endowed with a high percentage of voids due to pores with a diameter of more than 30 nm. Resistance to breakage of these catalysts compared with the corresponding solid-form catalysts is somewhat reduced.

EPA 355664 discloses catalysts for the oxidation of olefins and unsaturated aldehydes, in the form of thin rings equipped with radial reinforcing elements.

In EPA 464633 catalyst carriers based on noble metals (Pd, Au and others) are disclosed having a hollow cylindrical form endowed with one or more through-bores, wherein the diameter of the bores is at least 1 mm and the thickness of the wall is less than 1 mm. The dimensions of the cylinders are comprised between 3 and 10 mm in diameter and 2–10 mm in height.

The methodology of production of the heterogeneous catalysts is essentially of two types: one based on the technique of extrusion, and the other based on the technique of shaping by means of a compression (tableting).

The extrusion technique is indicated mostly for the production of granules of a simple form.

With this technique the active components are mixed in the form of a very viscous moist mass also containing a suitable extrusion lubricant uniformly distributed within the bulk to be extruded.

The catalysts and carriers disclosed in the patent literature reported above are prepared with the extrusion technique. Only the catalysts with a complex geometric shape described in U.S. Pat. No. 5,330,958 are prepared by tableting. The technique of tableting is, in fact, indicated mainly for the production of granules having a complex shape.

In this case the active components are mixed in the form of a powder to which a tableting lubricant is added and uniformly distributed in the mass to be tableted.

On the basis of what has been known up to now, tableting of powders for the production of catalyst granules is conditioned by the necessity of employing a high quantity of lubricant agent dispersed in the mass to be tableted (bulk lubrication), which give rise to several negative aspects:
embrittlement and collapse of the granule during the course of heat treatment activation of the catalysts, caused by the decomposition of the lubricating agent inside the granule;
variation in the porosity of the granule following the leakage of the lubricant during heat treatment;
possible chemical reactions between the lubricant and the active components of the catalyst during the heat treatment.

Possible local overheating due to insufficient lubrication of the walls subjected to greater friction concur in producing dishomogeneity in the characteristics of the granule and therefore in the performance of the catalyst.

The technique of tableting applied to the manufacture of granules for catalysts or carriers turns out to be more versatile than the extrusion technique but, as far as the state of the art developed so far is concerned, it presents unsurmountable limitations. In fact, due to the massive addition of lubricant necessary for the molding process, the essential parameters of the catalyst may undergo profound changes, such as mechanical resistance, resistance to abrasion, porosity, chemical composition, to the point of no longer being suitable for the function it is required to perform. After tableting, the catalyst particles undergo heat treatments specific to each type of catalyst, the purpose being the attainment of the catalyst components in an active form.

Moreover, very long treatment times are necessary for the elimination of the lubricant.

Tableting machines equipped with apparatus for the limited lubrication of the parts which come into contact with the powder to tableted have been in use for some time in the pharmaceutical field for the production of tablets. External lubrication ensures high machine productivity and allows for the production of tablets having considerable hardness characteristics.

Machines of this type are disclosed on U.S. Pat. No. 4,707,309 and are mainly employed in the production of medicinal tablets. Unlike tablets obtained through the use of a lubricant dispersed internally in the powder to be tableted (magnesium stearate), those obtained through external lubrication show marked characteristics of hardness due to the fact that the crystallites of the material making up the drug prove to be completely sintered amongst themselves.

The machine disclosed in U.S. Pat. No. 4,707,309 is also employed in the preparation of tablets for catalysts. The only example provided regards the preparation of a catalyst in the form of solid cylindrical tablets (8 mm in diameter and 5 mm in height), constituted of chromium oxide ($Cr_2O_3$) mixed with silica and hydrated aluminum oxide. The tablets obtained were not subjected to heat treatment activation.

Thanks to their marked characteristics of hardness, the use of cements, which are normally employed when tableting is carried out using an internal lubricant, is not required.

It has now been surprisingly found that it is possible to prepare, with high levels of productivity, catalyst and carrier granules having a regular geometric shape, but also a complex one and in particular, hollow cylindrical shape with circular, polygonal or multi-lobed section, endowed with remarkable characteristics of resistance to breakage and abrasion and with an optimum pore dimension and distribution.

The preparation of the granules is carried out by compression-shaping (tableting) the catalyst or carrier powder comprising the components of the catalyst or of the carrier or the catalyst or carrier precursors wherein, the lubricant is not dispersed in the powder mass to be tableted, but the lubricant is applied to those parts of the tableting apparatus which come into contact with the powder to be shaped (shaping chamber and the needles or punches employed in producing the through-bores). The tableted granules are then subjected to heat treatment activation wherein the active components of the catalyst are formed and the final characteristics of the porosity and distribution of the pores is developed.

For catalyst and carrier precursor it is meant a compound which, after heat treatment activation of the shaped granules, is converted into the active catalysts-forming component.

The catalysts and carriers obtained with the process of the invention show, compared with the corresponding catalysts prepared with tableting processes wherein the lubricant is dispersed in the bulk of the powder to be molded, improved properties of resistance to breakage and abrasion and optimum characteristics of porosity and distribution of the pores so as to ensure high catalytic performance, considerably superior to that of the catalysts obtained with processes of bulk lubrication. In particular, compared with catalysts and carriers obtained by bulk lubrication they show:

resistance to breakage and abrasion considerably superior (of at least 10% with respect to the corresponding catalyst or carrier obtained using 2.5% by weight of stearic acid as the internal lubricant; in the more favourable cases, resistance may arrive at values which are 2–3 times superior);

constancy in particle dimensions (in the catalysts and carriers obtained through bulk lubrication the sintering of a part or of all the particle, causes considerable deformation of the same;

increased porosity and surface area; the porosity is generally higher than 0.2 ml/g and the area more than 5 $m^2/g$;

limited distribution of the radius of the pores with absence or presence in a limited quantity, of the macroporosity present, in catalysts and carriers obtained by employing internal lubrication. The percentage of the volume of the pores having a radius corresponding to the pack values of the porosity distribution curve is higher than 65–70%.

By employing external lubrication, the lubricant is concentrated on the surface of the granule: the quantity employed is, therefore, much less than that required when the lubricant is dispersed in the whole bulk of the granule.

The quantity may be reduced from $1/10$ to $1/100$, by passing from bulk lubrication to surface lubrication.

As the lubricant is present only on the surface of the granule, the damaging changes that the lubricant may give rise to during the heat treatment activation, such as evaporation, sublimation, decomposition, oxygenation and possible reactions with the components of the catalyst are limited solely to the surface of the granule. The lengthy times of thermal treatment aimed at eliminating the lubricant employed in the course of bulk lubrication are no longer necessary. As has already been pointed out, external lubrication also allows for the increased productivity of the machine.

The lubricant dispersed in the granule bulk generally has a porogenic effect during heat treatment activation. It is surprising that, with the method of the invention wherein an internal lubricant is not employed, it is possible to obtain catalyst and carrier particles endowed with higher porosity values than in the case of bulk lubrication and that a very high percentage of the volume of the pores is made up of pores having a radius which corresponds to the peak values of the porosity distribution curve.

For example, in the case of cylindrical granules with a tri-lobed section with through-bores corresponding to the various lobes, obtained from $Fe_2(MoO_4)_3$ and $MoO_3$, the dimension and the distribution of the pores is such that at least 75% of the volume of the pores is made up of pores with a radius comprised between 1000 and 2000 Å.

On the other hand, the porosity characteristics in the case of the same catalyst obtained with the internal lubrication method are very different, in the sense that the distribution is widespread and, moreover, macroporosity is present.

The lubricants employed in the method of the invention comprise solids and liquids capable of reducing the friction coefficient between the powder to be tableted and those parts of the machine which come into contact with the same.

Examples of suitable lubricants are stearic and palmitic acid, alkaline salts and alkaline-earths of these acids such as, for example, magnesium, potassium or aluminum stearate; carbon black, talc, mono and triglycerides such as glycerine monostearate and monooleate, paraffin oil, perfluoropolyethers.

The liquid lubricants may be employed in solutions or dispersions in dispersing agents.

The quantity of liquid lubricants is in general comprised between 0.025 and 25 mg per granule.

The solid lubricants may be applied by dusting the molding chamber or any eventual punches, thereby covering them with a thin layer of lubricant powder carried by a continuous air flow.

The molding chamber and punches may be constructed or coated with self-lubricating materials, such as polytetrafluoroethylene or ceramic material. In this way, the use of external lubricants may be avoided or reduced.

The heat treatment to be effected on the granules after molding depends on the nature of the catalyst and carrier.

For example, in the case of $Fe_2(MoO_4)$ based catalysts, the heat treatment is comprised between 400° and 600° C.; in the case of catalysts for the production of styrene, the treatment is between 500° and 800° C., in the case of alumina, from 400° to 700° C.

It has been found, and this constitutes a further aspect of the invention, that external lubrication can be employed so as to selectively deposit components of the catalyst on the surface of the granule.

By means of this technique, it is possible to deposit, on the external surface of the catalyst, a thin layer enriched with one or more chemical compounds suitable for catalysis.

An asymmetric distribution of the active elements in the catalytic process can favour optimization of the use of the components themselves when these are preferentially deposited on the surface. In fact, in many chemical processes, in using heterogeneous catalysts the reactions preferably take place on the external surface of the granules because the phenomena of internal diffusion result to be limiting. Examples of active components that may be deposited on the surface of the granule are the catalysis promoters which can be introduced in the form of compounds constituting the lubricant or contained in the lubricant.

For example, MgO may be deposited on the granule surface of the catalyst by employing magnesium stearate as lubricant.

The catalysts of the invention are suitable for the catalysis of any kind of reaction realized by using the catalyst on a fixed bed.

Non-limiting examples of catalysts or catalyst carriers which can be prepared with the process of the invention, suitable for chemical processes and petroleum refining comprise:

catalysts for the oxidization of methanol to formaldehyde,
catalysts for the dehydrogenation of ethylbenzene to styrene,
catalysts for the oxychlorination of ethylene to dichloroethane,
catalysts for the isomerization of paraffin,
catalysts for the isomerization and hydrogenation of hydrocarbons of petrochemical use,
catalysts for the cracking and hydrocracking of petroleums,
catalysts for the hydrogenation of pyrolysis gasolines,
catalysts for naphtha reforming,
catalysts for the alkylation of aromatics,
catalysts for the hydrocracking of petroleums and bitumens,
catalysts for the dealkylation of aromatics,
catalysts for the desulfuration of petroleum fractions,
catalysts for the desulfuration of gas,
catalysts for the demetallation of petroleum fractions,
catalysts for the synthesis of ammonia,
catalysts for the synthesis of sulfur trioxide,
catalysts for the oxidation of $H_2S$ to sulfur,
catalysts for the production of synthesis gas,
catalysts for the conversion of water gas,
catalysts for the synthesis of methanol,
catalysts for the production of ethylene oxide,
catalysts for the production of vinyl acetate from ethylene,
catalysts for the production of vinyl acetate from acetylene
catalysts for the hydrogenation of acetylene,
catalysts for the hydrogenation of olefines,
catalysts for the hydrogenation of oils and fats,
catalysts for the hydrogenation of nitroderivatives,
catalysts for the hydrogenation of phenol to cyclohexanone,
catalysts for the purification of terephthalic acid,
catalysts for the production of oxygenated water,
catalysts for the production of phthalic anhydride,
catalysts for the production of maleic anhydride from benzene,
catalysts for the production of maleic anhydride from butane,
alumina based catalyst carriers.

The method of the invention is particularly suitable for the preparation of catalyst granules having a multi-lobed section, preferably tri-lobed, in which the through-bores have axes which are substantially parallel between themselves and to the axis of the granule and also substantially equidistant one from the other.

The ratio between the surface area and the volume of the granule in these catalysts is at least 2.4 when the lobes are substantially cylindrical and at least 3.1 when the section of the granule is substantially triangular with rounded extremities.

The following examples are provided purely by to illustrate but do not limit the invention in any way.

The volume of the pores was determined through mercury porosimetry; the surface area by B.E.T. method.

COMPARATIVE EXAMPLE 1

Figure 1:
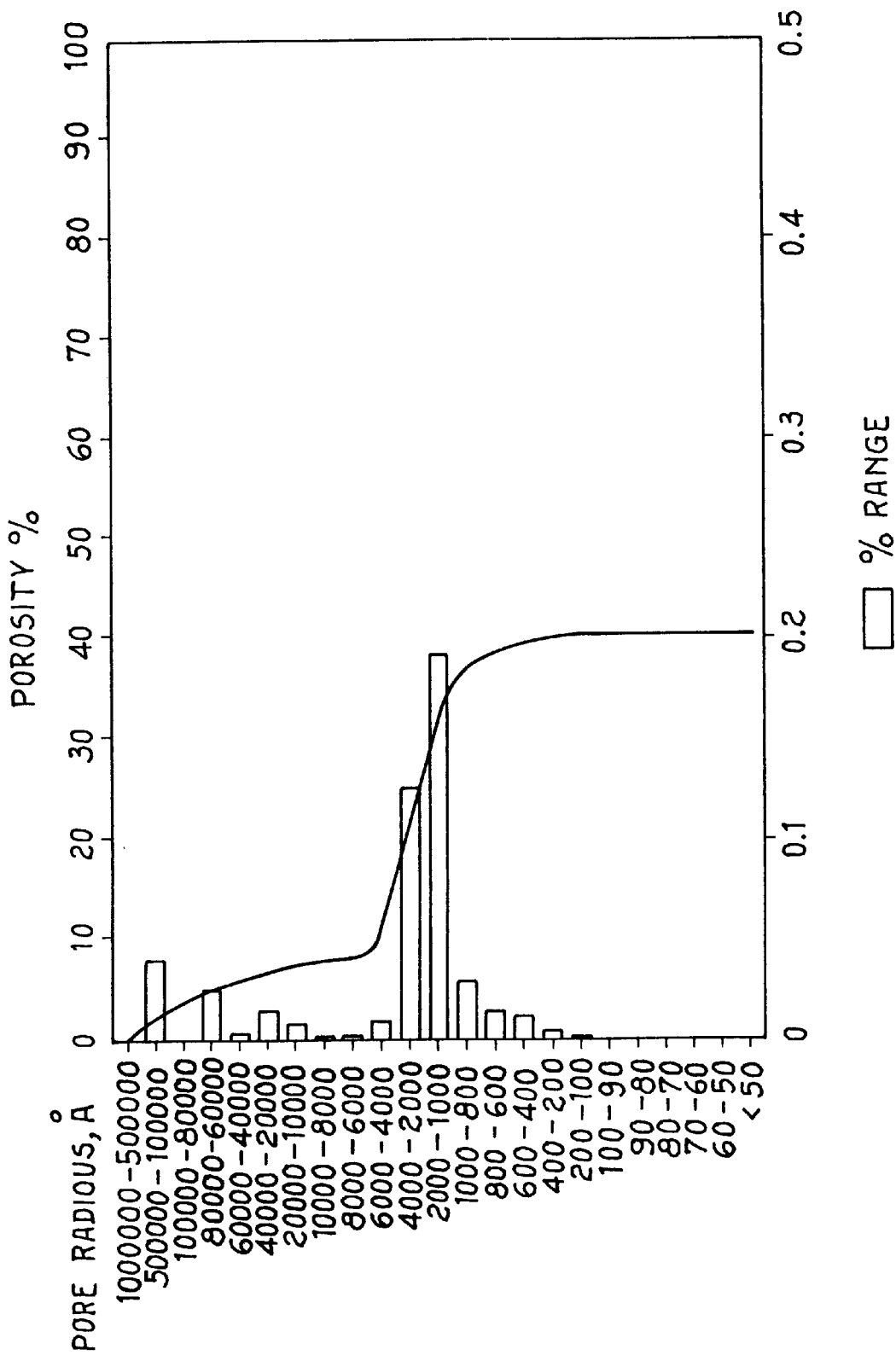
FIGS. 1–4 show the distribution of pores for catalysts of the invention.

A catalyst used for the oxidation of methanol to formaldehyde was prepared in conventional manner as follows: 97.5 g of a powder constituted of an intimate mixture of $Fe_2(MoO_4)_3$ and $MoO_3$ in a 2/1 molar ratio and granulometry comprised between 0.01 and 0.5 mm was mixed with 2.5 g of magnesium stearate used as a molding lubricant in a powder form having a granulometry lower than 140 mesh. After carefully homogenising the mixture, the powder was subjected to tableting using a FETTE mod. EXACTA E1 tableting machine, equipped with a holed trilobate punch having dimensions and geometric characteristics as reported in U.S. Pat. No. 5,330,959. The tri-lobed granules thus obtained had a diameter of 5.30 mm and a height of 4.5 mm. They were subjected to an activation process at 485° C. for 4 hours (the increase to 485° C. was obtained at a rate of 11° C./min; time 44 minutes). After cooling the tables displayed a dark green colour with signs of collapse, noticeable from the irregular dimensions; the number of the collapsed granules was noted and it was determined that more than 95% of the tablets did not conform to the dimensional norm. The breaking load, the surface area, the volume and the distribution of the pores of the tablets was then determined. the results are reported in table 1. FIG. 1 shows the distribution of the pores. Catalytic activity tests were then carried out on the same tablets using the method described hereinafter.

A vertical cylindrical reactor with an internal diameter of 20.4 mm and a height of 1900 mm equipped with an external fused-salt temperature bath, was loaded with catalyst granules to a height of 700 mm.

A gaseous flow was fed into the tubular reactor (with feeding from the top downwards) at a linear velocity of 1.5 Nm/sec and a total entry pressure of 950 mm Hg (1.25 bar). The methanol concentration was equal to 6% by volume, that of oxygen 10%, the remainder being nitrogen.

The temperature of the fused-salt bath was regulated in the range of between 250 to 280° C.

The reaction gasses, at the exit of the reactor, were analyzed by means of gas chromatography, utilizing two "Fractovap" gas chromatographies (model C.Erba). The first operated with a Porapak-T column which separated $CO_2$, $CH_2O$, OME (dimethylether) $H_2O$ and unconverted methanol; the second separated $O_2$, $N_2$, and CO using a molecular sieve column.

The results of the catalytic activity test are reported in table 2.

COMPARATIVE EXAMPLE 2

Figure 2:
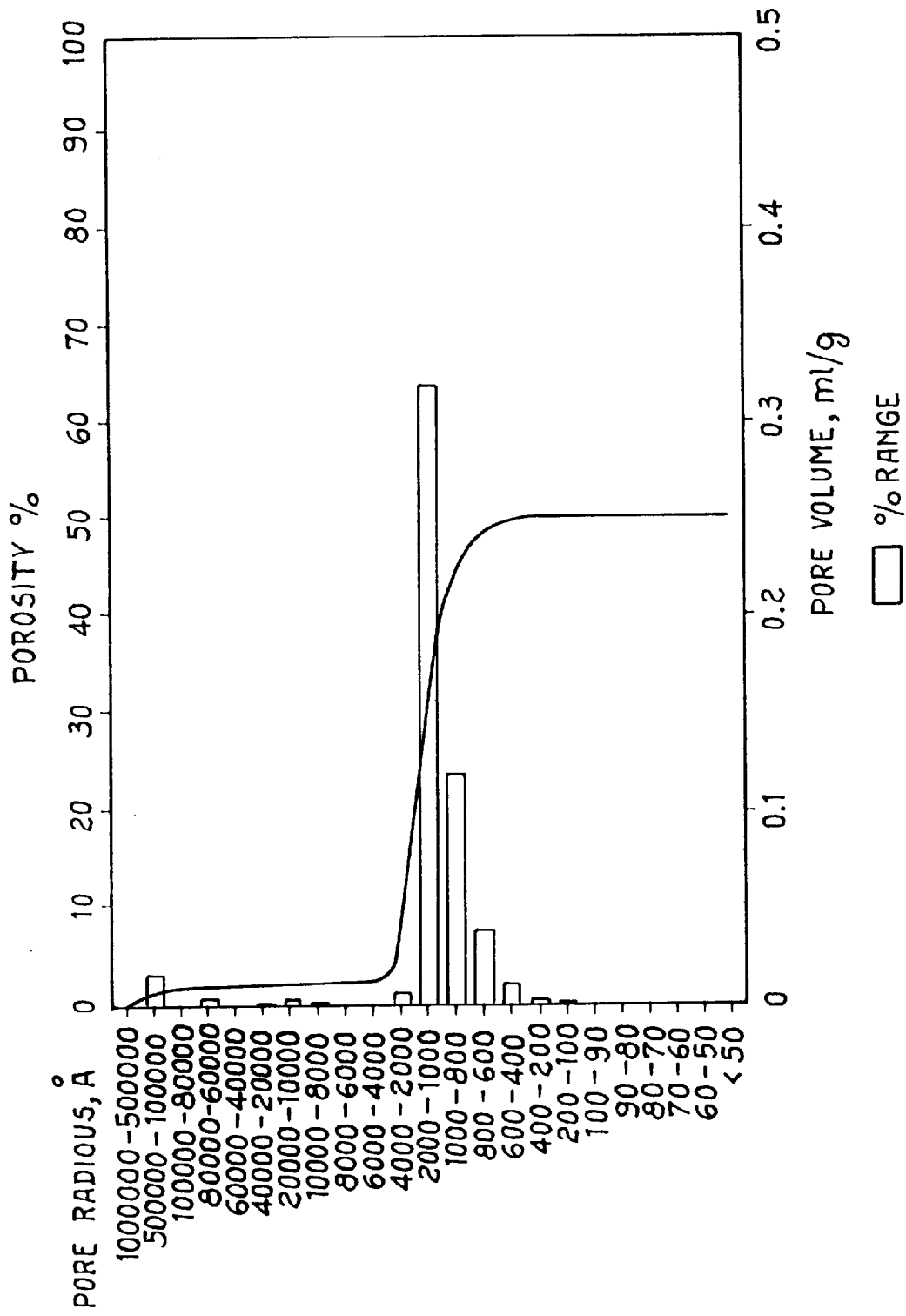

The same procedure was followed as in COMPARATIVE example 1, except that stearic acid was used in place of magnesium stearate as lubricating agent. In this case too, after heat treatment at 485° C., a marked collapse phenomenon in the tablets occurred: more precisely, 65.6% of the tablets turned out to have collapsed. The determination of the chemical-physical characteristics are summarized in table 1. FIG. 2 shows the distribution of the pores.

EXAMPLE 1

Figure 3:
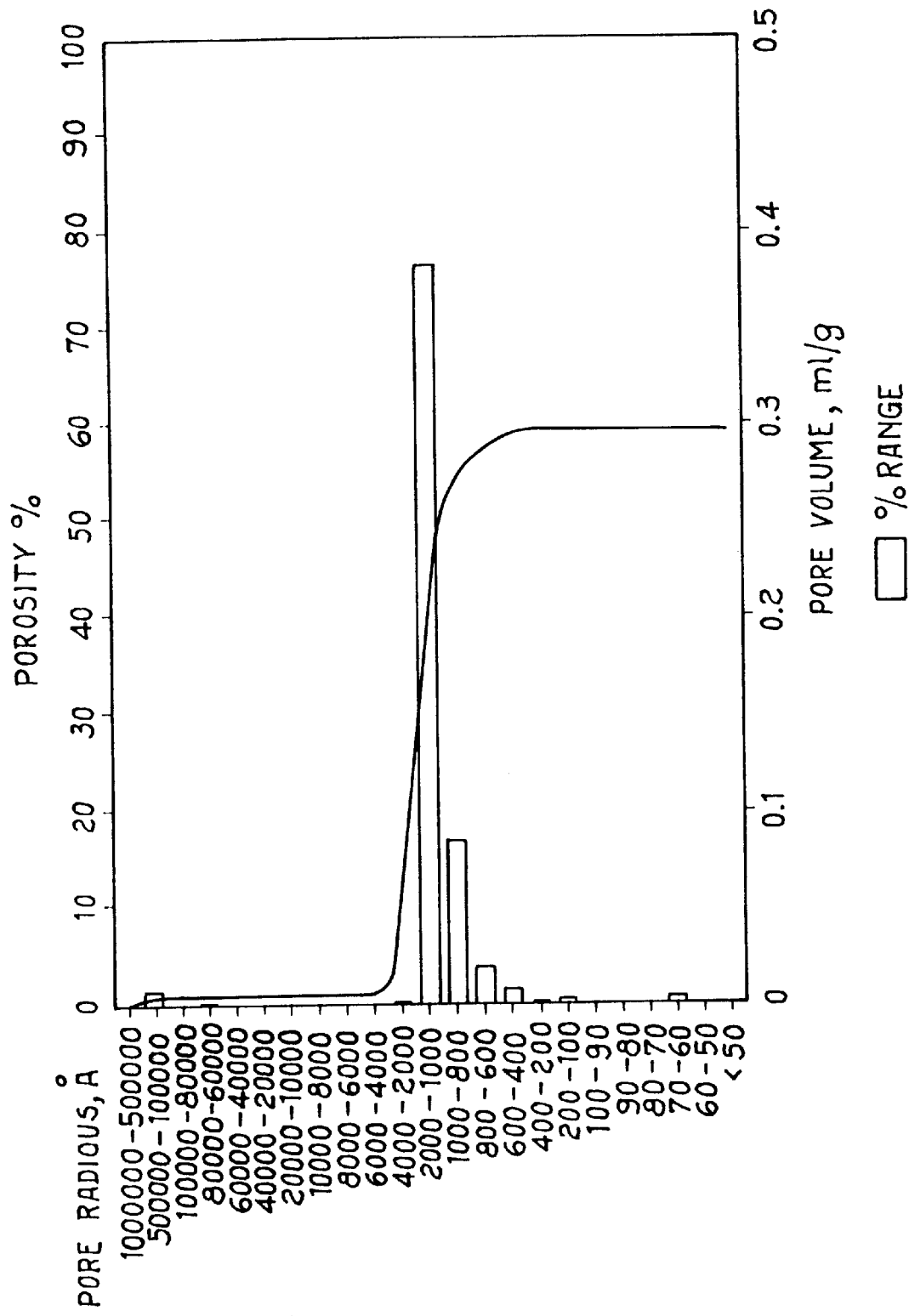

The same procedure was carried out as in comparative example 1, except that the magnesium stearate was used as a lubricant in the following manner:

the punches and the cylindrical chamber in which the tablet is shaped, were coated with a thin layer of magnesium stearate carried by a continuous air current. The air-flow was modified in a progressive manner with the purpose of obtaining efficient lubrication. After the molding of the catalyst tablets, they were activated in accordance with the standard procedure; 100% of the tablets proved to be regular, without any kind of deformation. The results of the characterizations are reported in table 1 and the catalytic activity data in table 2. FIG. 3 reports the distribution of the pores and the dimensional characteristics.

The advantage derived from the procedure of external lubrication compared to bulk lubrication is evident from the examination of the data. The tablets obtained with the method which is the subject of this invention show:

regular dimensions;

a clearly narrower distribution of the pores with macroporosity virtually absent;

larger surface areas;

higher porosity;

These conditions of porosity and dimensional regularity allow for the attainment of improved catalyst performance, as is shown in table 2.

EXAMPLE 2

The same procedure was carried out as in example 1, except that lubrication was carried out in the following manner:

magnesium stearate powder was compressed thereby producing a stearate tablet; one external lubrication cycle is effected (compression of the stearate powder) prior to each cycle of the compression of the catalytically active powder.

The results of the characterization tests are reported in table 1.

EXAMPLE 3

Figure 4:
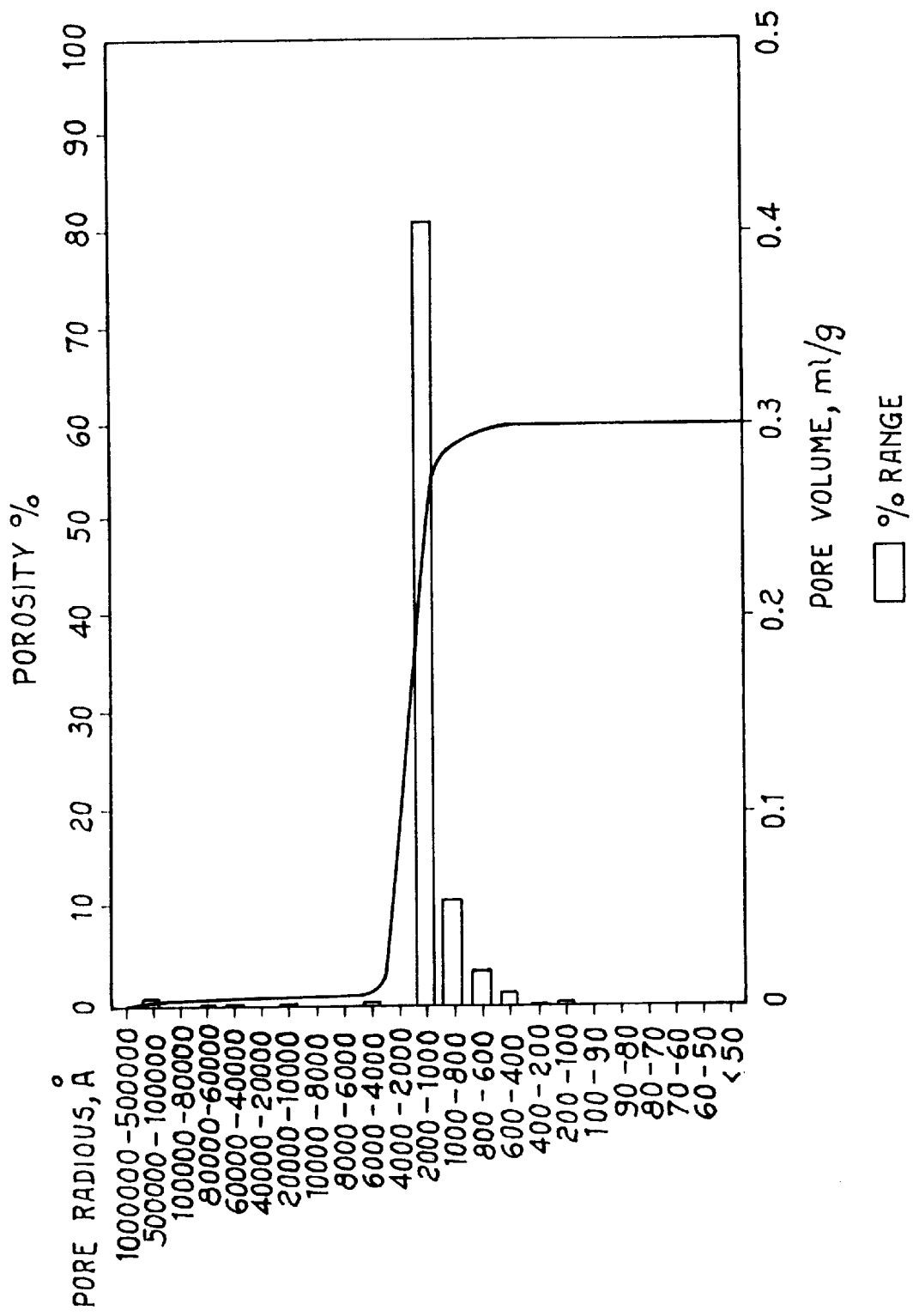

The same procedure was carried out as in example 1, but using stearic acid powder as the lubricating agent:

The results of the characterizing tests are reported in table 1. FIG. 4 shows the distribution of the pores.

TABLE 1

| TH | sinterized particles % | spec. area ($m^2/g$) | p.s. (g/ml) | p.s.a. (g/ml) | pore volume (ml/g) | average radious (Å) | axial braking load particle |
|---|---|---|---|---|---|---|---|
| Comparative example | 95.4 | 2.4 | 3.92 | 2.18 | 0.20 | 1667 | 8.4 ÷ 3.0 |
| Example No. 1 | 0.0 | 6.2 | 3.91 | 1.91 | 0.27 | 871 | 28 ÷ 5.9 |
| Example No. 2 | 0.0 | 7.1 | 3.93 | 1.85 | 0.29 | 817 | 31.2 ÷ 2.9 |
| Comparative Example 2 | 65.7 | 2.2 | 3.80 | 2.08 | 0.22 | 2000 | 18.5 ÷ 11.1 |
| Example No. 3 | 0.0 | 7.4 | 4.00 | 1.84 | 0.29 | 784 | 25 ÷ 2.5 | sint. = sinterised particles
p.s. = specific weight
p.s.a. = apparent specific weight

TABLE 2

CATALYTIC ACTIVITY TEST

Test conditions:
Concentration of $CH_3OH$, % vol. 6
Concentration of $O_2$, % vol. 10
Concentration of $N_2$, % vol. 84
Height of the catalytic bed, cm 70
Reactor diameter, mm 20.4

| CATALYST | TEMPERATURE SALT BATH ° C. | CONVERSION $CH_3OH$, % | MOLAR YIELD IN $CH_2O$; % |
|---|---|---|---|
| COMPARATIVE EXAMPLE 1 | 250 | 5.6 | 2.4 |
| | 260 | 28.2 | 25.1 |
| | 270 | 38.4 | 36.2 |
| | 280 | 42.3 | 38.9 |
| EXAMPLE 1 | 250 | 91.82 | 88.11 |
| | 260 | 96.73 | 92.86 |
| | 270 | 98.39 | 94.87 |

We claim:

1. A catalyst or catalyst carrier in the form of granules having a definite geometric shape provided with at least one through-bore, the catalyst or catalyst carrier being obtained by compression-shaping a powder comprising the catalyst or catalyst carrier components, or precursors thereof, wherein at least 70% of the volume of the pores stem from pores having a radius corresponding to the peak values of the porosity distribution curve, said powder comprising $Fe_2(MoO_4)_3$ and $MoO_3$.

2. A catalyst or catalyst carrier in the form of granules having a definite geometric shape provided with at least one through-bore, having resistance to breakage and abrasion at least 10% higher than that of corresponding catalysts or catalyst carriers in the form of granules obtained by compression shaping where lubrication during formation of the granules is carried out by employing a lubricant dispersed in a quantity of 3% by weight in the bulk of the powder to be subjected to shaping to form the granules.

3. The catalyst or catalyst carrier of claim 2, wherein the resistance to breakage and abrasion is at least three times that of corresponding catalysts or catalyst carriers in the form of granules obtained by compression shaping where lubrication during formation of the granules is carried out by employing a lubricant dispersed in a quantity of 3% by weight in the bulk of the powder to be subjected to shaping to form the granules.

4. A catalyst or catalyst carrier according to claim 1, wherein the granules have a hollow cylindrical form with a circular or polygonal or multi-lobed section with through-bores which have axes which are substantially parallel between themselves and to the axis of the granule and also substantially equidistant one from the other and wherein the ratio between the surface area and the volume of the granules is higher than 2.4.

5. A catalyst or catalyst carrier according to claim 2, wherein the granules have a hollow cylindrical form with a circular or polygonal or multi-lobed section with through-bores which have axes which are substantially parallel between themselves and to the axis of the granule and also substantially equidistant one from the other and wherein the ratio between the surface area and the volume of the granules is higher than 2.4.

6. The catalyst or catalyst carrier of claim 4, wherein the granules have a substantially triangular cross-section with rounded extremities and wherein the ratio between the surface area and the volume of the granules is higher than 3.1.

7. The catalyst or catalyst carrier of claim 4, wherein the granules have a tri-lobed cross-section.

8. The catalyst or catalyst carrier of claim 2, obtained from powders comprising $Fe_2(MoO_4)_3$ and $MoO_3$.

9. The catalyst or catalyst carrier of claim 1, obtained from powders comprising alumina.

10. The catalyst or catalyst carrier of claim 2, obtained from powders comprising alumina.

11. A process for the preparation of catalysts or catalyst carriers in the form of granules having a definite geometric shape provided with at least one through-bore, the catalyst or catalyst carrier being obtained by compression-shaping a powder comprising the catalyst or catalyst carrier components, or precursors thereof, wherein at least 70% of the volume of the pores stem from pores having a radius corresponding to the peak values of the porosity distribution curve, comprising the steps of:

(a) subjecting the powder or precursor to compression shaping using a lubricant, wherein the lubricant is deposited on the surface of the molding and shaping apparatus, to produce a granule; and (b) heating the granule from step (a) in order to activate the catalyst or catalyst carrier.

12. The process according to claim 11, wherein the lubricant is a solid selected from the group consisting of stearic acid, palmitic acid, and alkaline salts and alkaline-earth salts of said acids.

13. The process according to claim 11, wherein the lubricant is a liquid selected from the group consisting of glycerides, paraffin oil, and perfluoropolyethers.

14. The process according to claim 11, wherein the surface of the molding and shaping apparatus is self-lubricating.

15. A process according to claim 11, wherein the powder to be molded comprises $Fe_2(MoO_4)_3$ and $MoO_3$ and the granules obtained are subjected to heat treatment at temperatures from about 400° to about 600° C.

16. The catalyst or catalyst carrier of claim 2 which is substantially free of sintering.

17. The catalyst or catalyst carrier of claim 2 further comprising an axial braking load of at least 3.08.

* * * * *